United States Patent [19]

Fujimoto et al.

[11] Patent Number: 4,482,710

[45] Date of Patent: Nov. 13, 1984

[54] PROCESS FOR PREPARING 3-ALKOXYMETHYLCEPHALOSPORIN DERIVATIVES

[75] Inventors: Koichi Fujimoto; Eiji Nakayama; Hideo Nakao, all of Hiromachi, Japan

[73] Assignee: Sankyo Company Limited, Tokyo, Japan

[21] Appl. No.: 445,575

[22] Filed: Nov. 30, 1982

[30] Foreign Application Priority Data

Dec. 1, 1981 [JP] Japan .............................. 56-193461

[51] Int. Cl.$^3$ ............................................ C07D 501/04
[52] U.S. Cl. ...................................... 544/28; 544/29; 544/30
[58] Field of Search ............................. 544/30, 28, 29

[56] References Cited

U.S. PATENT DOCUMENTS 3,665,003  5/1972  Kennedy et al. ..................... 544/28

FOREIGN PATENT DOCUMENTS 0034536  8/1981  European Pat. Off. .............. 544/27

Primary Examiner—Paul M. Coughlan, Jr.
Attorney, Agent, or Firm—Frishauf, Holtz, Goodman & Woodward

[57] ABSTRACT

The acetoxymethyl group at the 3-position of 3-acetoxymethylcephalosporanic acids and salts thereof may be replaced by an alkoxymethyl group, by reacting the 3-acetoxymethylcephalosporanic acid or salt thereof with a $C_1$–$C_4$ alkanol in the presence of halide ions.

19 Claims, No Drawings

PROCESS FOR PREPARING 3-ALKOXYMETHYLCEPHALOSPORIN DERIVATIVES

BACKGROUND OF THE INVENTION

The present invention relates to a novel process for the preparation of 3-alkoxymethylcephalosporin derivatives from the corresponding 3-acetoxymethylcephalosporin derivatives.

Although many cephalosporin derivatives have been developed in recent years, often the practical, therapeutic use of these derivatives is delayed or prevented by problems with their production, and this may apply even where the derivatives are recognised to have valuable therapeutic activity.

The majority of cephalosporin derivatives elaborated by microorganisms possess an acetoxymethyl group at the 3-position. In the course or preparing therapeutically useful cephalosporin derivatives, it is often necessary to convert this acetoxymethyl group to other groups (generally substituted methyl groups), for example to alkoxymethyl groups. The following methods of preparing 3-alkoxymethylcephalosporin derivatives from the corresponding 3-acetoxymethylcephalosporin derivatives are known:

(A) The reaction of a 3-acetoxymethylcephalosporin derivative with a lower alkanol is described in U.S. Pat. No. 3,665,003. This process has the advantage of directly producing the desired 3-alkoxymethylcephalosporin derivative from the corresponding acetoxymethyl compound in a single step, but the yields obtained are very low and isolation and purification of the final product are difficult.

(B) Also described in said U.S. Pat. No. 3,665,003 is the preparation of 3-alkoxymethylcephalosporin derivatives by alkylating the corresponding 3-hydroxymethyl compound using a diazoalkane. This method also gives rise to some difficulties, in that the 3-acetoxymethyl group must first be converted to a 3-hydroxymethyl group, that the carboxy group at the 4-position must be protected and that diazoalkanes are toxic and dangerous to use; accordingly, it is undesirable to use large quantities of diazoalkanes, for example diazomethane. However, the yield from the alkylation step when using diazomethane in the presence of boron trifluoride is high. More conventional alkylating agents, such as methyl iodide, cannot be used, since these necessitate the conversion of the 3-hydroxymethyl group to a 3-sodiooxymethyl group and this conversion reaction inevitably gives rise to some damage to the β-lactam ring.

(C) U.S. Pat. No. 3,658,799 discloses the reaction of a 3-halomethyl compound with a lower alkanol to give the desired 3-alkoxymethylcephalosporin derivative. This reaction, however, requires three steps, including protection of the carboxy group at the 4-position, and the yields obtained in the reaction of the 3-halomethyl compound with the alkanol are not always good.

(D) U.S. Pat. No. 3,658,799 also discloses the reaction of a 3-haloacetoxymethylcephalosporin derivative with a lower alkanol. However, the preparation of the 3-haloacetoxymethyl compound used as starting material in this process from the original 3-acetoxymethyl compound requires three or four steps and, again, the yields obtained in the reaction with the alkanol are not good.

(E) 3-Alkoxymethylcelphalosporin derivatives can also be prepared by reacting a 3-halomethyl-2-cephem compound, with a lower alkanol to give a 3-alkoxymethyl-2-cephem compound, which is then isomerized to the desired 3-alkoxymethyl-3-cephem comound, as described in J. Med. Chem. 14,113 (1971). This method, however, requires many steps, as a 3-cephem compound, which is the compound originally obtained by fermentation, has first to be isomerized to the 2-cephem compound; the 3-methyl group of this compound has to be selectively halogenated; the compound is then reacted with the lower alkanol; and finally the 2-cephem compound has to be isomerized again to restore the 3-cephem compound; in addition, various of the substituent groups of the cephalosporin derivatives may need to be protected during one or more of these reactions.

In general, it is desirable to avoid multi-stage reactions, since the use of many reagents tends to make them expensive and since overall yields are generally rather low, as each additional reaction stage (unless the reaction takes place quantitatively, which is rare) leads to a reduction in overall yields.

For these reasons, although many cephalosporin derivatives having an alkoxymethyl group at the 3-position have been found to be valuable antibiotics, for example as described in U.S. patent application Ser. No. 304,988, filed Sept. 23, 1981, it is difficult to put them to practical use.

We have now discovered a method of converting the 3-acetoxymethyl group of 3-acetoxymethylcephalosporin derivatives to a 3-alkoxymethyl group in a single step and in relatively good yields.

The cephalosporin derivatives to which the process of the present invention is applied are compounds having a basic skeletal structure which may be represented as follows: T,0060
Such compounds have a carboxy group (or various derivatives of the carboxy group) at the 4-position. Compounds having a carboxy group at the 4-position are known as cephalosporanic acids or 3-cephem-4-carboxylic acids and are referred to as such herein. The compounds normally also have an amino group (or substituted amino group) and a hydrogen atom at the 7-position, although compounds having an alkoxy (generally methoxy) group at the 7-position and an amino or substituted amino group at the 7β-position are known.

BRIEF SUMMARY OF INVENTION

The present invention is concerned solely with the group at the 3-position of the cephalosporin derivative and provides a method of converting an acetoxymethyl group at this position to a lower alkoxymethyl group in a single step, which can (provided that it is carried out under the preferred conditions described hereafter) achieve relatively high yields of the final product, often exceeding 50%, which is regarded as very good in this field. The process of the invention will normally form one stage in the overall conversion of an original cephalosporin produced by fermentation to the desired therapeutically useful cephalosporin and the process of the invention may be carried out at any convenient stage in this overall process. Thus, the 3-alkoxymethylcephalosporin derivative produced by the process of the invention may itself have potent antibacterial activity and be of value for therapeutic use as an antibiotic or it may be an intermediate in the production of such a cephalosporin antibiotic.

Thus, the present invention provides a process for preparing a 3-alkoxymethylcephalosporanic acid or salt thereof, which comprises reacting a 3-acetoxymethylcephalosporanic acid or salt thereof with a $C_1$-$C_4$ alkanol in the presence of halide ions.

Surprisingly, the presence of halide ions in the reaction mixture enables the disadvantages of method (A) of the prior art discussed above to be overcome.

DETAILED DESCRIPTION OF INVENTION

The nature of the substituent at the 7-position of the 3-acetoxymethylcephalosporin starting material and hence the 3-alkoxymethylcephalosporin product is not critical to the present invention, provided that it does not participate in the reaction. Normally such a group will be a group of formula $R^1NH-$, in which $R^1$ represents a hydrogen atom or an organic group. The 3-acetoxymethylcephalosporanic acid in which $R^1$ represents a hydrogen atom is well known and is generally called "7-aminocephalosporanic acid" (7-ACA); it is well known as a starting material for a wide range of cephalosporin antibiotics. Alternatively, the group represented by $R^1NH-$ may be an acylamino group or a Schiff base, preferably an acylamino group.

Examples of the acyl group which may be represented by $R^1$ include: aliphatic acyl groups, such as the acetyl, propionyl, butyryl, isobutyryl, glutaryl, adipoyl and aminoadipoyl groups; aromatic acyl groups, such as the benzoyl, toluoyl or phthaloyl groups; aliphatic acyl groups having a substituent comprising an aromatic ring, such as the phenylacetyl or phenoxyacetyl groups; heterocyclic acyl groups, such as the oxazolylacetyl, thiazolylacetyl or thienylacetyl groups; and alkoxycarbonyl groups, such as the ethoxycarbonyl, t-butoxycarbonyl, benzyloxycarbonyl or trichloroethoxycarbonyl groups. The acyl moiety of these groups may be unsubstituted or may have one or more substituents, for example amino groups, hydroxy groups, halogen atoms, hydroxyimino groups, alkoxyimino groups, alkoxy groups, mercapto groups, alkylthio groups, oxo groups, sulphonyloxy groups or cyano groups; if desired, these substituents may be further protected with appropriate groups.

Examples of the Schiff bases include benzylideneamino groups, which are formed by the dehydration condensation of an aldehyde, such as benzaldehyde or salicyaldehyde, with an amino group.

Particularly preferred acyl groups which may be represented by $R^1$ include: phenoxyacetyl groups in which the benzene ring may be substituted or unsubstituted; haloacetyl groups; groups of formula $X-C_2.-C:O.C(:NOCH_3)C:O-$ in which X represents a halogen atom, a lower alkanesulphonyloxy group or a benzenesulphonyloxy group in which the benzene ring may be substituted or unsubstituted; and 2-(2-protected aminothiazol-4-yl)-2-methoxyiminoacetyl groups.

Most of the 3-acetoxymethylcephalosporin compounds used as starting materials are known, but, if they are new compounds, they may easily be prepared from cephalosporin C or 7-ACA by known methods.

The alkoxy group introduced into the cephalosporin compound in place of the acetoxy group by the process of the invention has from 1 to 4 carbon atoms and may be a straight or branched chain group, for example a methoxy, ethoxy, propoxy or isopropoxy group.

Since the group at the 4-position of the 3-acetoxymethylcephalosporin derivative used as starting material does not participate in the process of the invention, its nature is not critical. However, choice of the correct acid or salt can facilitate the reaction, for example by enabling the starting material to dissolve more readily in the chosen reaction solvent, or can facilitate recovery of the product from the reaction mixture. The salt may be a salt with ammonia, a metal or an organic base. Examples of suitable metals include alkali and alkaline earth metals, such as lithium, sodium, potassium or calcium, and examples of organic bases include primary, secondary and tertiary amines, such as triethylamine, dicyclohexylamine or t-octylamine. Usually, the sodium or potassium salt is preferred to facilitate the reaction, but the dicyclohexylamine salt is best for recovery of the reaction product. Accordingly, if desired, the salt employed during the reaction may be so chosen as to facilitate the reaction, e.g. the sodium or potassium salt, and this may then be converted, without any isolation or purification of the reaction product, to a salt, e.g. the dicyclohexylamine salt, chosen to facilitate recovery of the reaction product.

Surprisingly, the process of the invention is not applicable to esters of the 3-acetoxymethylcephalosporanic acids as an esterified carboxy group at the 4-position substantially reduces reactivity at the 3-position and prevents a reaction from taking place. However, if the desired final product is an ester, this may easily be obtained in good yield by a conventional esterification process from the salt obtained by the process of the invention.

The characteristic feature of the process of the invention is that the alkoxylation reaction is effected in the presence of a halide. In the absence of a halide, as can be seen from U.S. Pat. No. 3,665,003, yields are very low. On the other hand, when the reaction is carried out, in accordance with the present invention, in the presence of a halide, the reaction proceeds smoothly and the reaction rate increases by a factor of from 5 to 10, or even more.

There is no particular limitation on the nature of the halogen compound employed to generate the halide ions, provided that it is capable of generating halide ions in the reaction system chosen. Examples of such halogen compounds include: alkali metal halides, such as sodium chloride, lithium chloride, potassium chloride, lithium bromide, sodium bromide or potassium bromide; alkaline earth metal halides, such as calcium chloride or calcium bromide; halides of other metals, such as magnesium chloride or magnesium bromide; halides of organic bases, such as N-methylpyridinium chloride, tetramethylammonium chloride, tetrabutylammonium chloride, N-methylpyridinium bromide, tetramethylammonium bromide or tetraethylammonium bromide; and chloride or bromide salt-type resins of strongly basic quarternary ammonium ion-exchange resins, such as Dowex-I (Dowex is a trade mark). Metal halides, especially calcium chloride, magnesium chloride, sodium bromide, magnesium bromide and calcium bromide, are preferred and calcium chloride is most preferred, in view of its solubility in the preferred reaction media and its ready availability.

The amount of halogen compound employed may vary over a very wide range, depending upon the particular compound chosen, the reaction conditions and the reagents, but normally we prefer to employ it in an amount of from 1 to 20 times the weight of the 3-acetoxymethylcephalosporanic acid or salt thereof used as starting material.

The particular alkanol used in the process of the invention will depend upon the nature of the alkoxy group which it is desired should replace the acetoxy group in the 3-acetoxymethyl substituent; examples of suitable alkanols include methanol, ethanol, propanol, isopropanol and butanol. Of these, methanol is preferred, in view of its good reactivity and the excellent biological activities of most of the final compounds thus obtained.

The reaction will normally be carried out in an appropriate solvent, although the alkanol employed as a reagent may also function as the reaction solvent. Examples of other solvents include such polar liquids as acetone, acetonitrile, tetrahydrofuran, dimethylformamide, dimethylacetamide and water; mixtures of these solvents may also be employed. We have found that best results are achieved when the reaction is carried out in a medium comprising a mixture of the alkanol reagent with water. Water reduces the nucleophilic activity of the alkanol and thus protects the $\beta$-lactam moiety of the cephalosporanic acid. The concentration of the alkanol in the mixture of water and alkanol is preferably from 30 to 70% by volume; aqueous methanol in a concentration of from 30 to 70% by volume is particularly preferred.

The temperature at which the reaction is carried out is not critical to the present invention and accordingly, we prefer to carry out the reaction at a temperature which is sufficiently elevated to increase the rate of reaction but not so high as to cause degradation of the reagents or reaction products. A suitable temperature is in the range from 40° to 80° C. The time required for the reaction will depend upon many factors, including the reaction temperature, solvents and the particular halogen compound chosen, but the reaction will normally be complete within a period of from 0.5 to 10 hours.

After completion of the reaction, the desired product may be recovered from the reaction mixture by conventional means. For example, one suitable recovery sequence comprises: distilling off the organic solvent from the reaction mixture; adding water to the residue; adjusting the pH of the reaction mixture either to a value of from 2-3 (when there is a substituted amino group at the 7-position, i.e. $R^1$ represents an organic group) or a value of 6-7 (when there is a free amino group at the 7-position); and finally recovering the desired product by filtration of the precipitate thus formed or by extraction with a suitable organic solvent. If necessary, the desired product may be isolated in the form of an ester or, when there is a free amino group at the 7-position ($R^1$ represents a hydrogen atom), in the form of an acylated compound.

The invention is further illustrated by the following Examples, of which Examples 1-15 illustrate the process of the invention, Examples 16 and 17 illustrate the preparation of certain starting materials and Example 18 illustrates the use of one of the compounds obtained by the process of the invention for the preparation of a therapeutically useful cephalosporin antibiotic.

EXAMPLE 1

Dicyclohexylammonium
3-methoxymethyl-7-phenoxyacetamido-3-cephem-4-carboxylate 10 g of sodium 3-acetoxymethyl-7-phenoxyacetamido-3-cephem-4-carboxylate were dissolved in 100 ml of a 67% v/v aqueous methanol solution. 100 g of anhydrous calcium chloride were added to the solution, and then the mixture was stirred at 70° C. for 45 minutes. At the end of this time, 100 ml of ice-water, followed by 10 ml of 1N hydrochloric acid, were added to the reaction mixture. The reaction mixture was then extracted three times, each time with 100 ml of ethyl acetate. The extracts were combined, washed with an aqueous solution of sodium chloride and then extracted with two 50 ml portions of a 10% w/v aqueous solution of dipotassium phosphate. The extracts were combined, washed with a small amount of ethyl acetate and then acidified by the addition of a saturated aqueous solution of potassium hydrogen sulphate. The mixture was then extracted twice, each time with 100 ml of ethyl acetate. The ethyl acetate extracts were combined, washed with an aqueous solution of sodium chloride, dehydrated by the addition of anhydrous magnesium sulphate and then concentrated by evaporation under reduced pressure, to give 7.15 g of 3-methoxymethyl-7-phenoxyacetamido-3-cephem-4-carboxylic acid, in the form of a yellow solid.

This yellow solid was dissolved in 50 ml of ethyl acetate, and then 3.4 ml of dicyclohexylamine were added to the solution, and the resulting mixture was allowed to stand under ice-cooling for 2 hours. The crystals which precipitated were collected by filtration, washed with ethyl acetate and dried, to afford 8.43 g (yield 65.5%) of the title compound.

Nuclear Magnetic Resonance Spectrum (deuterodimethyl sulphoxide) $\delta$ppm: 0.8-2.3 (20H, multiplet); 2.7-3.4 (2H, multiplet); 3.18 (3H, singlet, methoxy); 3.38 (2H, singlet, $H_2$ at 2-position of cephem); 4.19 (2H, singlet, $CH_2$ at 3-position of cephem); 4.60 (2H, singlet, $CH_2$ of acetamido); 4.99 (1H, doublet, J=5.5 Hz, H at 6-position of cephem): 5.56 (1H, doubled doublet, J=5.5 and 9 Hz, H at 7-position of cephem); 6.7-7.5 (5H, multiplet, phenyl); 8.98 (1H, doublet, NH).

Infrared Absorption Spectrum (Nujol-trade mark-mull) $v_{max}$cm$^{-1}$: 2350-2700 $NH_2$ cation; 1770 =C=O, $\beta$-lactam; 1680 =C=O, amido.

EXAMPLE 2

Dicyclohexylammonium
3-methoxymethyl-7-phenoxyacetamido-3-cephem-4-carboxylate 2 g of sodium 3-acetoxymethyl-7-phenoxyacetamido-3-cephem-4-carboxylate were dissolved in 20 ml of 35% v/v aqueous methanol, and 16 g of sodium bromide were added to the resulting solution. The mixture was stirred at 70° C. for 2 hours, after which it was diluted with 20 ml of ice-water, neutralised by the addition of a saturated aqueous solution of sodium carbonate and then extracted twice, each time with 50 ml of ethyl acetate. The aqueous phase was acidified by the addition of a saturated aqueous solution of potassium hydrogen sulphate and then again extracted twice, each time with 50 ml of ethyl acetate. All of the ethyl acetate extracts were combined and the combined extracts were washed with an aqueous solution of sodium chloride, dehydrated over anhydrous magnesium sulphate and then concentrated by evaporation under reduced pressure to give 1.4 g of 3-methoxymethyl-7-phenoxyacetamido-3-cephem-4-carboxylic acid, in the form of a yellow solid.

The whole of this yellow solid was dissolved in 50 ml of ethyl acetate, and 0.73 ml of dicyclohexylamine was added to the solution. The resulting mixture was allowed to stand overnight at room temperature, after which the precipitate produced was collected by filtration, washed with ethyl acetate and dried, to give 1.18 g (yield 45.3%) of the title compound.

EXAMPLE 3

Dicyclohexylammonium 3-methoxymethyl-7-phenoxyacetamido-3-cephem-4-carboxylate 2 g of sodium 3-acetoxymethyl-7-phenoxyacetamido-3-cephem-4-carboxylate were dissolved in 20 ml of 35% v/v aqueous methanol, and 25 g of magnesium bromide hexahydrate were added to the solution. The resulting mixture was heated and stirred at 70° C. for 2 hours, after which it was treated as described in Example 2, to give 3-methoxymethyl-7-phenoxyacetamido-3-cephem-4-carboxylic acid in the form of a yellow solid.

The whole of this yellow solid was dissolved in 20 ml of ethyl acetate, and then 0.6 ml of dicyclohexylamine were added and the mixture was allowed to stand overnight at room temperature. The precipitate which formed was collected by filtration and dried, to give 590 mg (yield 22.6%) of the title compound.

EXAMPLE 4

Dicyclohexylammonium 3-methoxymethyl-7-phenoxyacetamido-3-cephem-4-carboxylate 2 g of sodium 3-acetoxymethyl-7-phenoxyacetamido-3-cephem-4-carboxylate were dissolved in 20 ml of 50% v/v aqueous methanol, and 20 g of magnesium chloride were added to the resulting solution. The mixture was then stirred at 70° C. for 1 hour, after which it was treated as described in Example 2, to give 1.4 g of 3-methoxymethyl-7-phenoxyacetamido-3-cephem-4-carboxylic acid, in the form of a yellow solid.

The whole of this yellow solid was dissolved in 50 ml of ethyl acetate, and 0.73 ml of dicyclohexylamine were added to the resulting solution. The mixture was allowed to stand overnight at room temperature, after which the crystals which precipitated were collected by filtration and dried, to give 1.16 g (yield 44.4%) of the title compound.

EXAMPLE 5

Dicyclohexylammonium 3-methoxymethyl-7-phenoxyacetamido-3-cephem-4-carboxylate 2 g of sodium 3-acetoxymethyl-7-phenoxyacetamido-3-cephem-4-carboxylate were dissolved in 20 ml of 50% v/v aqueous methanol, and 20 g of calcium bromide dihydrate were added to the resulting solution. The mixture was then stirred at 70° C. for 50 minutes, after which it was treated as described in Example 2, to give 1.55 g of 3-methoxymethyl-7-phenoxyacetamido-3-cephem-4-carboxylic acid, in the form of a yellow solid.

The whole of this yellow solid was dissolved in 50 ml of ethyl acetate, and 0.81 ml of dicyclohexylamine were added to the solution. The mixture was allowed to stand at room temperature for 3 hours, and the resulting precipitate was collected by filtration, washed with ethyl acetate and dried, to give 1 g (yield 38.4%) of the title compound.

EXAMPLE 6

7-[2-(2-Chloroacetamidothiazol-4-yl)-2-(Z)-methoxyiminoacetamido]-3-methoxymethyl-3-cephem-4-carboxylic acid 5 g of 3-acetoxymethyl-7-[2-(2-chloroacetamidothiazol-4-yl)-2-(Z)-methoxyiminoacetamido]-3-cephem-4-carboxylic acid and 800 mg of sodium hydrogen carbonate were dissolved in 50 ml of 70% v/v aqueous methanol. 75 g of anhydrous calcium chloride were added to the solution, and the mixture was stirred at 70° C. for 1 hour. The mixture was then diluted with 100 ml of ice-water, acidified by the addition of 1 ml of concentrated hydrochloric acid, and extracted three times, each time with 100 ml of ethyl acetate. The extracts were combined and the combined extracts were extracted three times, each time with 50 ml of a 10% w/v aqueous solution of dipotassium phosphate. The extracts were combined and the combined extracts were washed with a small amount of ethyl acetate, acidified with a saturated aqueous solution of potassium hydrogen sulphate, and extracted twice with 100 ml portions of ethyl acetate and then once with 50 ml of ethyl acetate. The extracts were combined and the combined extracts were washed with an aqueous solution of sodium chloride, dehydrated over anhydrous magnesium sulphate and concentrated by evaporation under reduced pressure. When the volume of the mixture had reduced to about 50 ml, the evaporation was stopped, as crystals began to precipitate. The concentrate was first heated to redissolve the crystals and then ice-cooled and allowed to stand for 3 hours. The resulting crystals were collected by filtration, washed with ethyl acetate and dried, to give 3.01 g (yield 63.5%) of the title compound.

Nuclear Magnetic Resonance Spectrum (deuterodimethyl sulphoxide) $\delta$ ppm: 3.27 (3H, singlet, methoxy of methoxymethyl); 3.60 (2H, singlet, $H_2$ at 2-position of cephem); 3.97 (3H, singlet, methoxy of methoxyimino); 4.26 (2H, singlet, $CH_2$); 4.43 (2H, singlet, $CH_2$); 5.25 (1H, doublet, J=5 Hz, H at 6-position of cephem); 5.89 (1H, doubled doublet, J=5 and 9 Hz, H at 7-position of cephem); 7.50 (1H, singlet, H of aminothiazole ring); 9.83 (1H, doublet, J=9 Hz, NH).

EXAMPLE 7

Dicyclohexylammonium 7-benzyloxycarbonylamino-3-methoxymethyl-3-cephem-4-carboxylate 2.5 g of sodium 3-acetoxymethyl-7-benzyloxycarbonylamino-3-cephem-4-carboxylate were dissolved in 25 ml of 66% v/v aqueous methanol, and 25 g of anhydrous calcium chloride were added to the mixture. The mixture was stirred at 70° C. for 1 hour, after which it was diluted with 50 ml of ice-water, its pH was adjusted to a value of 1–2 by the addition of hydrochloric acid and it was extracted twice, each time with 50 ml of ethyl acetate. The extracts were combined, washed with aqueous solution of calcium chloride, dehydrated over anhydrous magnesium sulphate and then concentrated by evaporation under reduced pressure. The concentrate was dissolved in 20 ml of ethyl acetate, and then 1.7 g of dicyclohexylamine were added thereto. The mixture was left to stand, with ice-cooling, for 3 hours. The crystals which were produced were collected by filtration and dried, to give 2.1 g (yield 64.2%) of the title compound.

Nuclear Magnetic Resonance Spectrum (CDCl$_3$) $\delta$ ppm: 0.8–2.4 (20H, multiplet); 2.7–3.4 (2H, multiplet); 3.27 (3H, singlet, methoxy); 3.42 (2H, singlet, $H_2$ at 2-position of cephem); 4.32 (2H, singlet, $CH_2$ at 3-position of cephem); 4.9–5.2 (2H, multiplet, H at 6- and 1-positions of cephem); 5.08 (2H, singlet, $CH_2$ of benzyl); 5.3–5.6 (3H, multiplet, H at 7-position of cephem and 2H of dicyclohexylammonium); 7.29 (5H, singlet, phenyl).

EXAMPLE 8

Dicyclohexylammonium 7-chloroacetamido-3-methoxymethyl-3-cephem-4-carboxylate 2 g of 3-acetoxymethyl-7-chloroacetamido-3-cephem-4-carboxylic acid and 483 mg of sodium hydrogen carbonate were dissolved in 20 ml of 60% v/v aqueous methanol, and 30 g of anhydrous calcium chloride were added. The mixture was then stirred at 70° C. for 50 minutes, after which it was diluted with 50 ml of ice-water, its pH was adjusted to a value of 1-2 by the addition of hydrochloric acid, and it was extracted three times, each time with 50 ml of ethyl acetate. The ethyl acetate extracts were combined, washed with an aqueous solution of sodium chloride, dehydrated over anhydrous magnesium sulphate and concentrated by evaporation under reduced pressure to give 1.3 g of 7-chloroacetamido-3-methoxymethyl-3-cephem-4-carboxylic acid in an impure state as an amorphous solid.

30 ml of ethyl acetate were added to this solid, and then active carbon was added for decolouration. The carbon was filtered off, and 735 mg of dicyclohexylamine were added to the filtrate, to precipitate colourless crystals. The filtrate was ice-cooled, left to stand for 3 hours and then filtered. The crystals were washed with ethyl acetate and then dried, to give 1.56 g (yield 54%) of the title compound.

Nuclear Magnetic Resonance Spectrum ($CDCl_3$) $\delta$ ppm: 0.7-2.4 (20H, multiplet); 2.7-3.4 (2H, multiplet); 3.28 (3H, singlet, methoxy); 3.42 (2H, singlet, $H_2$ at 2-position of cephem); 4.06 (2H, singlet, $CH_2$ of chloroacetamido); 4.29 (2H, singlet, $CH_2$ at 3-position of cephem); 4.96 (1H, doublet, J=5.5 Hz, H at 6-position of cephem); 5.62 (1H, doubled doublet, J=5.5 and 9 Hz, H at 7-position of cephem); 7.15 (1H, doublet, J=9 Hz, NH).

EXAMPLE 9

7-Isobutyrylamino-3-methoxymethyl-3-cephem-4-carboxylic acid 2 g of 3-acetoxymethyl-7-isobutyrylamino-3-cephem-4-carboxylic acid and 490 mg of sodium hydrogen carbonate were dissolved in 21 ml of 66% v/v aqueous methanol, and 30 g of calcium chloride dihydrate were added. The resulting mixture was stirred at 70° C. for 90 minutes, after which it was cooled and 40 ml of water and 50 ml of ethyl acetate were added. The aqueous phase was adjusted to a pH value of 7-8 and separated, after which it was acidified with hydrochloric acid and extracted three times, each time with 50 ml of ethyl acetate. The extracts were combined, and the combined extracts were washed with an aqueous solution of sodium chloride, dehydrated over anhydrous magnesium sulphate and concentrated by evaporation under reduced pressure. The residue was dissolved in a small volume of ethyl acetate, and insolubles were filtered off. Diisopropyl ether was added to the filtrate, and the resulting precipitates were collected by filtration and dried, giving 800 mg (yield 43.5%) of the title compound.

Nuclear Magnetic Resonance Spectrum (deuteroacetone) $\delta$ ppm: 1.10 (3H, doublet, J=7 Hz, $CH_3$ of isobutyryl); 1.15 (3H, doublet, J=7 Hz, $CH_3$ of isobutyryl); 2.3-3.0 (1H, multiplet, CH of isobutyryl); 3.20 (3H, singlet, methoxy); 3.63 (2H, singlet, $H_2$ at 2-position of cephem); 4.22 (2H, singlet, $CH_2$ at 3-position of cephem); 5.01 (1H, doublet, J=5 Hz, H at 6-position of cephem); 5.60 (1H, doubled doublet, J=5 and 8 Hz, H at 7-position of cephem); 8.04 (1H, doublet, J=8 Hz, NH).

EXAMPLE 10

7-[2-(2-Formylaminothiazol-4-yl)-2-methoxyiminoacetamido]-3-methoxymethyl-3-cephem-4-carboxylic acid 1 g of sodium 3-acetoxymethyl-7-[2-(2-formylaminothiazol-4-yl)-2-methoxyiminoacetamido]-3-cephem-4-carboxylate were dissolved in 12 ml of 50% v/v aqueous methanol, and 20 g of calcium chloride dihydrate were added. The mixture was then stirred at 70° C. for 35 minutes, after which it was diluted with 30 ml of ice-water and insolubles were filtered off. The filtrate was acidified with hydrochloric acid and extracted three times, each time with 50 ml of ethyl acetate. The extracts were combined, washed with an aqueous solution of sodium chloride, dehydrated over anhydrous magnesium sulphate and concentrated by evaporation under reduced pressure. The residue was dissolved in ethyl acetate, and diethyl ether was added thereto. The resulting solid was separated, giving 0.6 g (yield 66.7%) of the title compound.

Nuclear Magnetic Resonance Spectrum (deuteroacetone) $\delta$ ppm: 3.27 (3H, singlet, methoxy of methoxymethyl); 3.55 (2H, singlet, $H_2$ at 2-position of cephem); 3.88 (3H, singlet, methoxy of methoxyimino); 4.27 (2H, singlet, $CH_2$ at 3-position of cephem); 5.10 (1H, doublet, J=5 Hz, H at 6-position of cephem); 5.75 (1H, doubled doublet, J=5 and 8 Hz, H at 7-position of cephem); 7.31 (1H, singlet, H of thiazole); 8.42 (1H, singlet, formyl); 9.57 (1H, doublet, J=8 Hz).

EXAMPLE 11

3-Methoxymethyl-7-(4-methoxyphenoxyacetamido)-3-cephem-4-carboxylic acid 2 g of sodium 3-acetoxymethyl-7-(4-methoxyphenoxyacetamido)-3-cephem-4-carboxylate were dissolved in 20 ml of 60% v/v aqueous methanol, and 20 g of calcium chloride dihydrate were added to the resulting solution. The mixture was stirred at 70° for 50 minutes, after which it was diluted with 40 ml of ice-water, its pH was adjusted to a value of 6-7, and it was extracted with two separate 50 ml portions of ethyl acetate. The aqueous phase was adjusted to a pH value of 1-2 by the addition of hydrochloric acid, and it was then extracted three times, each time with 50 ml of ethyl acetate. The extracts were combined, and the combined extracts were washed with an aqueous solution of sodium chloride, dehydrated over anhydrous magnesium sulphate and then concentrated by evaporation under reduced pressure, to give 1.7 g of a solid containing the title compound in an impure form-yield 95% of theory, before purification.

Nuclear Magnetic Resonance Spectrum (deuteroacetone) $\delta$ ppm: 3.26 (3H, singlet, methoxy); 3.57 (2H, singlet, $H_2$ at 2-position of cephem); 3.73 (3H, singlet, methoxy); 4.29 (2H, singlet, $CH_2$ at 3-position of cephem); 4.59 (2H, singlet, $CH_2$ of acetamido); 5.07 (1H, doublet, J=5 Hz, H at 6-position of cephem); 5.79 (1H, doubled doublet, J=5 and 9 Hz, H at 7-position of cephem); 6.85 (4H, singlet, phenyl); 8.03 (1H, doublet, J=9 Hz, NH).

EXAMPLE 12

3-Methoxymethyl-7-(3-oxobutyrylamino)-3-cephem-4-carboxylic acid 1.43 g of 3-acetoxymethyl-7-(3-oxobutyrylamino)-3-cephem-4-carboxylic acid and 0.34 g of sodium hydrogen carbonate were dissolved in 15 ml of 67% v/v aqueous methanol, and 21.5 g of calcium chloride dihydrate were added. The mixture was then stirred at 70° C. for 1 hour, after which it was diluted with 30 ml of ice-water, its pH was adjusted to a value of 1–2 by the addition of hydrochloric acid, and it was extracted three times, each time with 50 ml of ethyl acetate. The extracts were combined and the combined extracts were extracted twice, each time with 20 ml of a 5% w/v aqueous solution of dipotassium phosphate. The pH of the combined extracts was adjusted to a value of 1–2 by the addition of hydrochloric acid, and the mixture was then again extracted twice, each time with 50 ml of ethyl acetate. The combined extracts were washed with an aqueous solution of sodium chloride, dehydrated over anhydrous magnesium sulphate and then concentrated by evaporation under reduced pressure, to give 0.95 g (yield 72%) of a yellow solid containing the title compound.

Nuclear Magnetic Resonance Spectrum (deuterodimethyl sulphoxide) $\delta$ ppm: 2.14 (3H, singlet, $CH_3$); 3.27 (3H, singlet, methoxy); 3.49 (2H, singlet, $H_2$ at 2-position of cephem); 3.55 (2H, singlet, $CH_2$); 4.29 (2H, singlet, $CH_2$ at 3-position of cephem); 5.04 (1H, doublet, J=5 Hz, H at 6-position of cephem); 5.65 (1H, doubled doublet, J=5 and 8 Hz, H at 7-position of cephem); 8.72 (1H, doublet, J=8 Hz, NH).

EXAMPLE 13

Dicyclohexylammonium-3-methoxymethyl-7-phenoxyacetamido-3-cephem-4-carboxylate 5 g of 7-aminocephalosporanic acid and 3.1 g of sodium hydrogen carbonate were dissolved in 50 ml of 66% v/v aqueous methanol, and 75 g of anhydrous calcium chloride were added. The mixture was then stirred at 70° C. for 1.5 hours, after which it was cooled, 100 ml of water and 50 ml of acetone were added, and the mixture was ice-cooled. To the mixture was then added dropwise, with stirring, a solution of 3.75 g of phenoxyacetyl chloride in 20 ml of acetone and the mixture was allowed to stand at room temperature for 30 minutes. The mixture was then concentrated by evaporation under reduced pressure to about two thirds of its original volume, and then 200 ml of ethyl acetate and hydrochloric acid were added. The mixture was extracted twice, each time with 100 ml of ethyl acetate. The extracts were combined, washed with an aqueous solution of sodium chloride, dehydrated over anhydrous magnesium sulphate and then concentrated by evaporation under reduced pressure. The residue was dissolved in about 30 ml of ethyl acetate, and insolubles were filtered off. 3 g of dicyclohexylamine were added to the filtrate, and the mixture was left to stand for 30 minutes at room temperature and then for 3 hours with ice-cooling. The crystals which were produced were collected by filtration and dried, giving 2.1 g (yield 20.4%) of the title compound.

Nuclear Magnetic Resonance Spectrum (deuterodimethyl sulphoxide) $\delta$ ppm: 0.8–2.3 (20H, multiplet); 2.7–3.4 (2H, multiplet); 3.18 (3H, singlet, methoxy); 3.38 (2H, singlet, $H_2$ at 2-position of cephem); 4.19 (2H, singlet, $CH_2$ at 3-position of cephem); 4.60 (2H, singlet, $CH_2$ of acetamido); 4.99 (1H, doublet, J=5.5 Hz, H at 6-position of cephem); 5.56 (1H, doubled doublet, J=5.5 and 9 Hz, H at 7-position of cephem); 6.7–7.5 (5H, multiplet, phenyl); 8.98 (1H, doublet, NH).

EXAMPLE 14

7-[4-Chloro-3-oxo-(Z)-2-methoxyiminobutyrylamino]-3-methoxymethyl-3-cephem-4-carboxylic acid 500 mg of 3-acetoxymethyl-7-[4-chloro-3-oxo-(Z)-2-methoxyiminobutyrylamino]-3-cephem-4-carboxylic acid and 150 mg of sodium hydrogen carbonate were dissolved in 5 ml of 67% v/v aqueous methanol, and 5 g of anhydrous calcium chloride were added thereto. The resulting mixture was stirred at 65° C. for 1 hour, after which 30 ml of ice-water and 50 ml of ethyl acetate were added to the reaction mixture. The mixture was then acidified with hydrochloric acid and the aqueous phase was separated. The aqueous phase was then extracted twice, each time with 30 ml of ethyl acetate. The extracts were combined, and the combined extracts were washed with an aqueous solution of sodium chloride, dried over anhydrous magnesium sulphate, and then concentrated by evaporation under reduced pressure, to give 320 mg of the title compound, in the form of a pale solid.

Nuclear Magnetic Resonance Spectrum (deuterodimethyl sulphoxide) $\delta$ ppm: 3.20 (3H, singlet, methoxy of methoxymethyl); 3.50 (2H, singlet, $H_2$ at 2-position of cephem); 4.02 (3H, singlet, methoxy of methoxyimino); 4.15 (2H, singlet, $CH_2$ at 3-position of cephem); 4.77 (2H, singlet, $CH_2$ of chlorobutyryl); 5.08 (1H, doublet, J=5 Hz, H at 6-position of cephem); 5.70 (1H, doubled doublet, J=5 and 9 Hz, H at 7-position of cephem); 9.34 (1H, doublet, J=9 Hz, NH).

EXAMPLE 15

7-[4-Methanesulphonyloxy-3-oxo-(Z)-2-methoxyiminobutyrylamino]-3-methoxymethyl-3-cephem-4-carboxylic acid 510 mg of 3-acetoxymethyl-7-[4-methanesulphonyloxy-3-oxo-(Z)-2-methoxyiminobutyrylamino]-3-cephem-4-carboxylic acid and 130 mg of sodium hydrogen carbonate were dissolved in 5.1 ml of 67% v/v aqueous methanol, and 5.1 g of anhydrous calcium chloride were added. The mixture was stirred for 1 hour at a bath temperature of 70° C., after which 50 ml of ice-water were added and the mixture was acidified to a pH value of 1.0 by the addition of hydrochloric acid. The mixture was then extracted with ethyl acetate. The extract was washed with an aqueous solution of sodium chloride and dried over anhydrous magnesium sulphate, after which the solvent was distilled off, giving 352 mg of the title compound in the form of a pale brown, foamy substance.

Nuclear Magnetic Resonance Spectrum (deuteroacetone) $\delta$ ppm: 3.18 (3H, singlet, $CH_3$ of methanesulphonyl); 3.28 (3H, singlet, methoxy of methoxymethyl); 3.53 (broad singlet, $H_2$ at 2-position of cephem); 4.08 (3H, singlet, methoxy of methoxyimino); 4.23 (2H, singlet, $CH_2$ at 3-position of cephem); 5.09 (1H, doublet, J=5 Hz, H at 6-position of cephem); 5.27 (2H, singlet, $CH_2$ of sulphonyloxybutyryl); 5.78 (1H, doubled doublet, J=5 and 9 Hz, H at 7-position of cephem); 8.30 (1H, doublet, J=9 Hz, NH at 7-position of cephem).

EXAMPLE 16

3-Acetoxymethyl-7-(3-oxobutyrylamino)-3-cephem-4-carboxylic acid 5.44 g of 7-aminocephalosporanic acid were dissolved in 20 ml of a 1N aqueous solution of sodium hydroxide, and 1.68 g of diketene were added, with ice-cooling, to the resulting solution. The mixture was stirred at the same temperature for 1 hour, after which it was diluted with 20 ml of ethyl acetate and then acidified. The mixture was extracted twice with ethyl acetate and the combined extracts were washed with an aqueous solution of sodium chloride, dehydrated over anhydrous magnesium sulphate and then concentrated by evaporation under reduced pressure, giving 4.4 g of the title compound as crystals melting at 150° C. (with decomposition).

Nuclear Magnetic Resonance Spectrum (deuterodimethyl sulphoxide) δ ppm: 2.02 (3H, singlet); 2.15 (3H, singlet); 3.41 (2H, singlet); 3.53 (2H, singlet); 4.78 (2H, AB-quartet, J=12 Hz); 5.03 (1H, doublet, J=5 Hz); 5.60 (1H, doubled doublet, J=5 and 8 Hz); 8.92 (1H, doublet, J=8 Hz).

EXAMPLE 17

3-Acetoxymethyl-7-[4-methanesulphonyloxy-3-oxo-2-(Z)-methoxyiminobutyrylamino]-3-cephem-4-carboxylic acid 0.54 ml of dimethylformamide and 0.65 ml of phosphorous oxychloride were heated together at 40° C. for 1 hour. The mixture was cooled, and then 30 ml of methylene chloride were added, after which the solvents were distilled off. 30 ml of dry ethyl acetate were added to the residue, followed by 2.75 g of dicyclohexyl ammonium 4-methanesulphonyloxy-3-oxo-2-methoxyiminobutyrate (syn form), and the mixture was stirred for 5 minutes at room temperature.

Meanwhile, 1.9 g of 7-aminocephalosporanic acid and 6.3 ml of bis(trimethylsilyl)acetamide were dissolved in 30 ml of dry ethyl acetate, and the solution was cooled to −30° C. The whole of the above-prepared mixture containing the dicyclohexyl ammonium salts was then added, in a single portion, to the cooled solution, and the mixture was stirred for 1.67 hours at a temperature ranging from −10° C. to 0° C. The mixture was then washed, in turn, with dilute hydrochloric acid and water, and then dried over anhydrous magnesium sulphate. The solvent was distilled off, giving 1.4 g of the title compound in the form of a pale brown, foamy substance.

Nuclear Magnetic Resonance Spectrum (deuteroacetone) δ ppm: 2.03 (3H, singlet, $CH_3$ of acetoxy); 3.17 (3H, singlet, $CH_3$ of methanesulphonyl); 3.55 (2H, AB-quartet, J=18 Hz, $H_2$ at 2-position of cephem); 4.09 (3H, singlet, methoxy of methoxyimino); 4.90 (2H, AB-quartet, J=13 Hz, $CH_2$ at 3-position of cephem); 5.09 (1H, doublet, J=5 Hz, H at 6-position of cephem); 5.28 (2H, singlet, $CH_2$ of sulphonyloxybutyryl); 5.81 (1H, doubled doublet, J=5 and 9 Hz, H at 7-position of cephem); 8.37 (1H, doublet, J=9 Hz, NH at 7-position).

EXAMPLE 18

1-Isopropoxycarbonyloxyethyl 7-[2-(2-aminothiazol-4-yl)-(Z)-2-methoxyiminoacetamido]-3-methoxymethyl-3-cephem-4-carboxylate This Example is included to illustrate the preparation of a therapeutically useful compound from a compound prepared by the process of the invention (the compound prepared as described in Example 14).

210 mg of 7-[4-chloro-3-oxo-(Z)-2-methoxyiminobutyrylamino]-3-methoxymethyl-3-cephem-4-carboxylic acid were dissolved in 2 ml of dimethylacetamide, and 100 mg of dicyclohexylamine and 150 mg of 1-iodoethyl isopropylcarbonate were added, with ice-cooling. After 30 minutes, 50 ml of ethyl acetate were added, and the mixture was washed, in turn, with 1N hydrochloric acid, water and an aqueous solution of sodium chloride. The mixture was then dried over anhydrous magnesium sulphate and concentrated by evaporation under reduced pressure. The residue was chromatographed through a column of silica gel eluted with a 1:1 by volume mixture of ethyl acetate and cyclohexane, to give a mixture of 1-isopropoxycarbonyloxyethyl 7-[4-chloro-3-oxo-(Z)-2-methoxyiminobutyrylamino]-3-methoxymethyl-3-cephem-4-carboxylate and 1-isopropoxycarbonyloxyethyl 7-[4-iodo-3-oxo-(Z)-2-methoxyiminobutyrylamino]-3-methoxymethyl-3-cephem-4-carboxylate. This mixture was dissolved in a mixture of 2 ml of dimethylacetamide and 1 ml of a phosphate buffer solution (pH 6.86), and then 60 mg of thiourea and 60 mg of sodium iodide were added, and the whole mixture was stirred for 3 hours. At the end of this time, 50 ml of ethyl acetate were added to the reaction mixture, which was then washed, in turn, with a 5% aqueous solution of sodium thiosulphate and an aqueous solution of sodium chloride. The mixture was dried over anhydrous magnesium sulphate and concentrated by evaporation under reduced pressure. The residue was dissolved in a small volume of ethyl acetate, and then diisopropyl ether was added to give a precipitate, which was collected by filtration and dried, giving 200 mg of the title compound in the form of a powder.

Nuclear Magnetic Resonance Spectrum ($CDCl_3$) δ ppm: 1.30 (6H, doublet, J=6 Hz, 2 methyls of isopropyl); 1.56 (3H, doublet, J=5.5 Hz, $CH_3$ of carbonyloxyethyl); 3.30 (3H, singlet, methoxy of methoxymethyl); 3.52 (2H, singlet, $H_2$ at 2-position of cephem); 4.00 (3H, singlet, methoxy of methoxyimino); 4.30 (2H, singlet, $CH_2$ at 3-position of cephem); 4.5–5.1 (1H, multiplet, CH of isopropyl); 5.00 (1H, doublet, J=5 Hz, H at 6-position of cephem); 5.3–5.8 (2H, broad singlet, $NH_2$); 5.8–6.2 (1H, multiplet, H at 7-position of cephem); 6.68 (1H, singlet, H at 5-position of thiazole); 6.6–7.1 (1H, multiplet, CH of carbonyloxyethyl); 7.7–8.0 (1H, multiplet, NH at 7-position).

We claim:

1. A process for preparing a 3-alkoxymethylcephalosporanic acid or salt thereof, which comprises reacting a 3-acetoxymethylcephalosporanic acid or salt thereof with a $C_1$–$C_4$ alkanol in the presence of halide ions selected from the group consisting of chloride ions and bromide ions, said halide ions being generated by a halogen compound selected from the group consisting of alkali metal chlorides and bromides, and alkaline earth metal chlorides and bromides, said halogen compound being in an amount of from 1 to 20 times the weight of said 3-acetoxymethylcephalosporanic acid or salt thereof.

2. The process as claimed in claim 1, wherein said halide ions are generated by a compound selected from the group consisting of calcium chloride, magnesium chloride, sodium bromide, magnesium bromide and calcium bromide.

3. The process as claimed in claim 1, wherein said halide ions are generated by calcium chloride.

4. The process as claimed in claim 1, wherein said alkanol is selected from the group consisting of methanol, ethanol, propanol, isopropanol and butanol.

5. The process as claimed in claim 1, wherein said alkanol is methanol.

6. The process as claimed in claim 1, wherein the reaction is effected in a reaction medium comprising said alkanol.

7. The process as claimed in claim 1, wherein the reaction is effected in a reaction medium comprising a solvent selected from the group consisting of acetone, acetonitrile, tetrahydrofuran, dimethylformamide, dimethylacetamide and water.

8. The process as claimed in claim 1, wherein the reaction is effected in the presence of an aqueous alkanol as reaction medium.

9. The process as claimed in claim 1, wherein the reaction is effected in the presence of, as reaction medium, an aqueous alkanol having a concentration of from 30 to 70% by volume.

10. The process as claimed in claim 1, wherein the reaction is effected in the presence of, as reaction medium, aqueous methanol having a concentration of from 30 to 70% by volume.

11. The process as claimed in claim 1, wherein said cephalosporanic acid has a group of formula $R^1NH-$ at the 7-position, wherein $R^1NH-$ represents an amino group, an acylamino group or a Schiff base.

12. The process as claimed in claim 11, wherein $R^1$ represents a group selected from phenoxyacetyl groups (in which the benzene ring is substituted or unsubstituted), haloacetyl groups, groups of formula $X-CH_2-C:O.C(:NOCH_3)C:O-$ (wherein X represents a halogen atom, a lower alkanesulphonyloxy group or a benzenesulphonyloxy group wheren the benzene ring is substituted or unsubstituted) and 2-(2-protected aminothiazol-4-yl)-2-methoxyiminoacetyl groups.

13. A process for preparing a 3-alkoxymethylcephalosporanic acid or salt thereof, which comprises reacting a 3-acetoxymethylcephalosporanic acid having at its 7-position a group of formula $R^1NH-$ (wherein $R^1$ represents a hydrogen atom or an organic group) or a salt thereof with a $C_1-C_4$ alkanol in the presence of halide ions selected from the group consisting of chloride ions and bromide ions, employing a mixture of said alkanol and water as the reaction medium, said halide ions being generated by a halogen compound selected from the group consisting of alkali metal chlorides and bromides, and alkaline earth metal chlorides and bromides, said halogen compound being in an amount of from from 1 to 20 times the weight of said 3-acetoxymethylcephalosporanic acid or salt thereof.

14. The process as claimed in claim 13, wherein said alkanol is methanol.

15. The process as claimed in claim 13, wherein the concentration of said alkanol in said water is from 30 to 70% by weight.

16. The process as claimed in claim 13, wherein said alkanol is methanol and is present in said reaction medium to a concentration of from 30 to 70% by weight.

17. The process as claimed in claim 13, wherein said halide ions are generated by calcium chloride.

18. A process for preparing a 3-alkoxymethylcephalosporanic acid or salt thereof, which comprises reacting a 3-acetoxymethylcephalosporanic acid or salt thereof with a $C_1-C_4$ alkanol in an aqueous medium and in the presence of a metal halide selected from the group consisting of calcium chloride, magnesium chloride, sodium bromide, magnesium bromide and calcium bromide.

19. A process as claimed in claim 18, wherein said metal halide is calcium chloride.

* * * * *